US00PP11327P

United States Patent [19]

Boyle, III

[11] Patent Number: Plant 11,327

[45] **Date of Patent: *Apr. 4, 2000**

[54] CACTACEAE PLANT NAMED 'AVALON'

[75] Inventor: Thomas H. Boyle, III, Amherst, Mass.

[73] Assignee: University of Massachusetts, Boston, Mass.

[ * ] Notice: This patent is subject to a terminal disclaimer.

[21] Appl. No.: 09/062,824

[22] Filed: Apr. 20, 1998

[51] Int. Cl.[7] ..... A01H 5/00

[52] U.S. Cl. ..... Plt./372

[58] Field of Search ..... Plt./372

[56] References Cited

PUBLICATIONS

Boyle et al., *J. Amer. Soc. Hort. Sci.,* 119(5):1060–1067, 1994.

Barthlott et al., *Bradleya,* 13:43–79, 1995.

*Primary Examiner*—Howard J. Locker
*Assistant Examiner*—Melissa L. Kimball
*Attorney, Agent, or Firm*—Fish & Richardson, P.A., P.C.

[57] ABSTRACT

A new and distinct plant variety of the Cactaceae family arising as a spontaneous mutation of *Hatiora×graeseri* 'Evita', is distinguishable from its progenitor and related varieties by its larger flowers, larger pollen grains, larger and thicker phylloclades, reduced branching, and a flower longevity of about 8 days. The new variety is a stable periclinal cytochimera with a diploid epidermis and tetraploid subepidermis. The new variety exhibits greater resistance to stem breakage due to its more robust phylloclades.

2 Drawing Sheets

The invention relates to a new and distinct plant variety of the Cactaceae family that has been named *Hatiora×graeseri* 'Avalon' by the inventor.

Several species of the Cactaceae family are commercially grown as flowering potted plants, including asexually-propagated varieties of the genus *Hatiora* [=*H. gaertneri, H. rosea,* and their interspecific hybrids (=*H.×graeseri*)]. The genus Hatiora is commonly known as Easter cactus. In the northern hemisphere, varieties of Easter cactus flower predominantly in March, April, and May; flowering plants are marketed from late winter until late spring. Among the various Hatiora varieties in cultivation is Hatiora 'Evita', a diploid variety with a chromosome number of 2n=22. Flowers of 'Evita' are about 5.6 cm in diameter with perianth-segments (undifferentiated sepals and petals) that are up to 6.7 mm in width and 33 mm in length. Perianth-segments of 'Evita' are predominantly cyclamen purple (Royal Horticultural Society 74 B/C) and flower longevity is about 11 to 12 days. 'Evita' is male and female fertile but highly self-incompatible, so that fruit set is rarely attained when flowers are self-pollinated.

An objective of the invention has been to develop a robust variety of Easter cactus with large cyclamen-purple flowers that would be distinguishable from known related varieties and have an acceptable flower longevity for marketing purposes. The objectives of the invention have been attained by the discovery of the spontaneous mutation described in detail herein. The new plant variety was discovered as a spontaneous mutation on a plant of 'Evita' growing in a greenhouse at Amherst, Mass. The progenitor variety, 'Evita', has been in general commerce in the United States.

Stem cuttings were taken from the mutated branch and were rooted at the same greenhouse. Several cycles of asexual reproduction demonstrated that the mutation was stable and reproduced true-to-type.

The 'Avalon' variety arose as a spontaneous bud mutation of 'Evita', yielding a stable cytochimera with a diploid epidermis and a tetraploid (2n=44) subepidermis. This cytochimera has remained stable through at least eight cycles of asexual propagation from stem cuttings. No revertants to the diploid state have been observed.

The 'Avalon' variety exhibits many improved characteristics over its progenitor. Flowers of 'Avalon' are substantially larger and more ornamental than those of 'Evita'. 'Avalon' is self-compatible and will set fruit when flowers are self-pollinated, whereas 'Evita' is self-incompatible and does not set fruit when the flowers are self-pollinated. Phylloclades of 'Avalon' are larger and thicker than those of 'Evita'. Plants of 'Avalon' are less branched than those of 'Evita'. However, 'Avalon' and 'Evita' are essentially identical in flower color and phylloclade color.

Through successive asexual propagation cycles, it has been ascertained that the new plant variety 'Avalon' is:

1) clearly distinguishable from its progenitor ('Evita') or any other Hatiora variety known to the inventor; and 2) uniform and stable, i.e., all relevant characteristics remained unchanged through asexual reproduction. The new plant variety exhibits the following principal traits:

1. Phylloclades that are longer and wider than those of its progenitor.

2. A more erect, stiffer plant that is less prone to stem breakage than its progenitor.

3. A plant that exhibits less branching compared to its progenitor, with comparisons made on either pruned or unpruned plants. On unpruned plants, 'Avalon' typically produces two to three new phylloclades per segment whereas 'Evita' produces three to four new phylloclades per segment.

4. Flowers that are considerably larger (about 6.7 cm in diameter) compared to those of its progenitor (about 5.6 cm in diameter).

5. Flowers that remain open about 8 days, which is about 3 to 4 days less than those of its progenitor 'Evita' (11 to 12 days).

The accompanying photographs illustrate the new plant variety.

Figure 1:
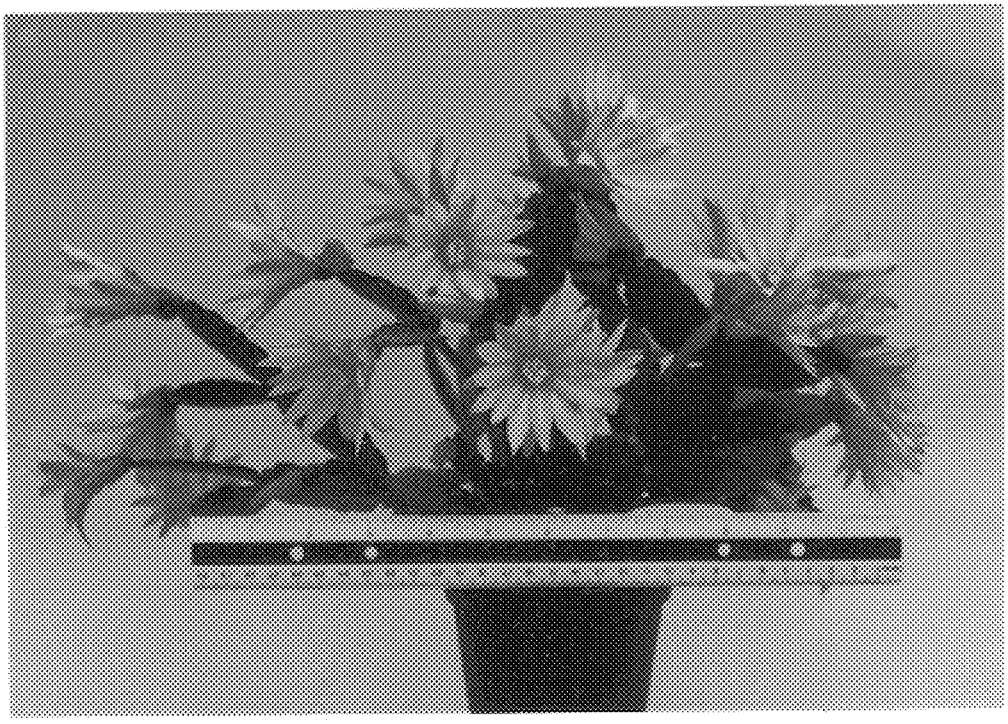
FIG. 1 is a color photograph of a 14-month-old flowering plant of the new plant variety that was propagated in winter.
Figure 2:
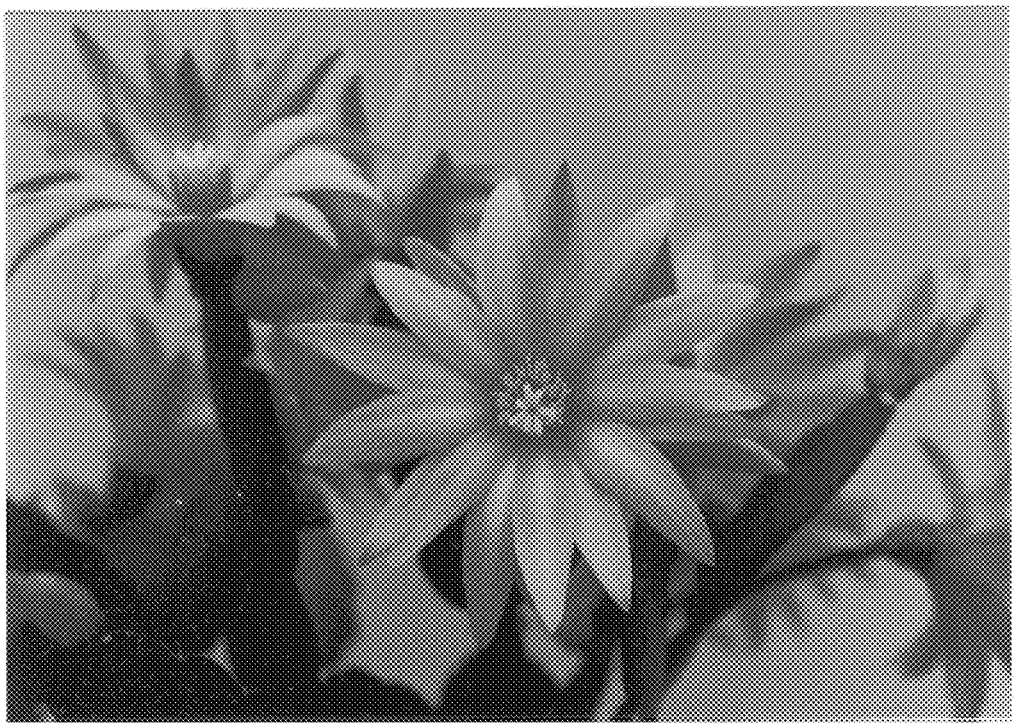
FIG. 2 is a color photograph showing a close-up view of flowers on the 14-month-old plant of FIG. 1.
Figure 3:
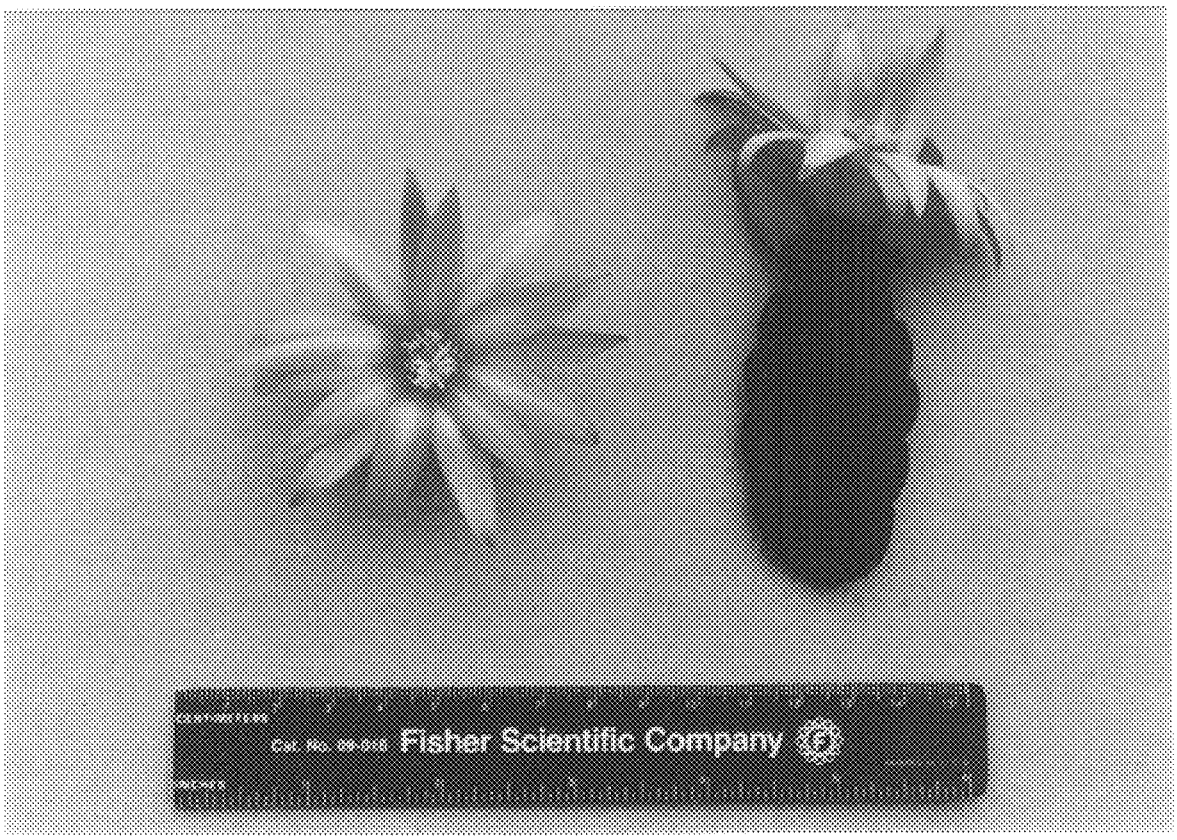
FIG. 3 is a color photograph showing close-up views of flowers and phylloclades of the new plant variety.

The following is a detailed description of the new plant variety, including the color(s) of each plant part. Color was characterized qualitatively using The Royal Horticultural Society (R.H.S.) Colour Chart. Fully expanded flowers and phylloclades were compared with the R.H.S. Colour Chart to determine color chip(s) closest to the respective color. Color names were obtained from the Table of Cross References that is supplied with the R.H.S. Colour Chart. The plants described herein were grown using standard horticultural practices and were less than 20-months-old from the time of initial propagation. Plants were grown at Amherst, Mass., in shaded greenhouses (≈2,000 footcandles light intensity) with a temperature regime of 60° F. nights/70–80° F. days. Plants were fertilized at each watering with 225 ppm nitrogen (N) using a 15% N—16% $P_2O_5$—17% $K_2O$ fertilizer. Flower longevity was measured on plants grown in a growth chamber at a constant temperature of 20° C.

DETAILED PLANT DESCRIPTION

I. Name: *Hatiora×graeseri* 'Avalon'.

II. Parentage: spontaneous mutation of *Hatiora×graeseri,* a non-patented variety known commercially as 'Evita'. 'Evita' has phylloclades that are narrower in width and shorter in length than 'Avalon'. In addition, 'Evita' has smaller flowers with narrower and shorter perianth-segments. In addition, 'Evita' exhibits greater branching and has longer-lasting flowers than 'Avalon'.

III. Classification:

A. *Botanic.*—(reference: W.Barthlott and N.P. Taylor. 1995. Notes towards a monograph of Rhipsalideae (Cactaceae). Bradleya 13:43–79). (1) Family: Cactaceae. (2) Tribe: Rhipsalideae. (3) Genus: Hatiora Britton & Rose (formerly Rhipsalidopsis). (4) Subgenus: Rhipsalidopsis (Britton & Rose) Barthlott. (5) Species: ×*graeseri* Barthlott ex D. Hunt [=interspecific hybrids of *H. gaertneri* (Regel) Barthlott and *H. rosea* (Lagerheim) Barthlott].

B. *Commercial.*—Easter cactus.

IV. Form: A shade-loving, succulent tropical perennial that exhibits a strictly determinate growth pattern and produces a series of leafless, elliptic-oblong stem segments (phylloclades) with crenate margins. Plants in natural settings are either epiphytic or lithophytic.

V. Stems:

A. *General.*—Stems are comprised of a series of leafless, elliptic-oblong segments (phylloclades) with crenate margins and (usually) an oblique base. Phylloclades are usually flatted but may occasionally be angular with 3 to 4 ribs. Axillary buds (areoles) restricted to margins and apices of phylloclades. At the apex, areoles are crowded together to form a "composite" areole, whereas areoles that develop below the apex are solitary. New phylloclades and flowers develop almost exclusively from composite areoles. Phylloclades are capable of forming adventitious roots.

B. *Phylloclades.*—(1) General: Succulent, elliptic-oblong, determinate, and (usually) flat with a composite areole at the apex, 4- to 5-crenate along the margins with an areole in each notch, and an oblique base. Areoles produce setaceous spines from 0.5 to 10 mm in length. (2) Midrib: (a) General — Extends longitudinally from base to apex and comprised of a cylinder of pith surrounded by branching network of vascular tissue. Prominent only in dried specimens. (b) Texture —Succulent, glabrous to slightly coriaceous with a waxy epidermis when recently mature, and becoming corky and woody with age. (c) Size (at maturity) — 1. Length: Usually between 50 and 70 mm and averaging about 60 mm. 2. Thickness: Usually between 3 and 5 mm at the midrib and averaging about 4 mm. (d) Color (at maturity) — Usually moderate olive green (R.H.S. 137 B/C). (3) Margins: (a) General — 4- to 5-crenate from base to apex and moderately tapered from midrib to margins. (b) Texture — Succulent, with a glabrous to slightly coriaceous epidermis when recently mature, and becoming corky and woody with age. (c) Size (at maturity) — 1. Thickness: About 1–2 mm in the area adjacent to the margin. 2. Width: Usually between 14 and 16 mm as measured from the midrib to the most offset marginal areole and averaging about 15 mm. Usually 10 to 13 mm distance between adjacent marginal areoles and averaging about 12 mm. 3. Color (at maturity): Beetroot purple (R.H.S. 71A). The pigmented area averages 2- to 3-mm in width and forms a continuous band around the margin of the phylloclade. (4) Teeth: none. (5) Areoles: (a) Composite (apical) areole — Usually 6 to 14 mm in length (averaging about 10 mm) and 1 to 2 mm in width, producing setaceous spines from 0.5 to 10 mm in length. New phylloclades and flowers develop almost exclusively from composite areoles. (b) Axillary (lateral) areoles — Usually 0.5 to 1.0 mm in diameter with setaceous spines from 0.5 to 3 mm in length.

VI. Flowers:

A. *General.*—Sessile, actinomorphic, perfect, epigynous, and developing predominately on the composite areoles of apical phylloclades. Perianth-segments 20 to 25, margins entire, the outermost perianth-segments subulate, the innermost perianth-segments linear-lanceolate and slender-acute. Perianth-tube short. Stamens numerous, inserted in one series at the base of the perianth. Stigma lobes 6 to 8 and usually 7. Ovary obconic, naked, and 4- to 7-angled (usually 5). Flowers nyctinastic and odorless.

B. *Perianth-segments.*—(1) General: about 20 to 25, inserted on top of ovary, margins entire. The outermost perianth-segments subulate. The innermost perianth-segments linear-lanceolate and slender-acute. Perianth-segments scarcely united at the base, more or less spreading. Color at anthesis — Cyclamen purple (R.H.S. 74 B/C).

C. *Androecium* (*stamens*).—(1) General: Inserted in one close series at the base of the perianth, inclined towards the center of the flower, anthers producing viable pollen. (2) Stamen number: About 185 to 200. (3) Filaments: (a) General — Short, capillary, terete, and glabrous. (b) Shape — Short, capillary, terete. (c) Texture — Glabrous. (d) Color (at anthesis) — Cyclamen purple (R.H.S. 74A). (e) Size (fully expanded flower) — 1. Length: Between 8 and 14 mm and usually 12 mm. 2. Diameter: Usually about 0.2 mm at insertion and tapering to about 0.1 mm at distal end. (4) Anthers: (a) General — Four longitudinally dehiscent pollen sacs arising from a connective by which they are attached to the filament. (b) Shape — Oblong. (c) Texture — Waxy. (d) Color (at maturity) Aureolin (R.H.S. 12A). (e) Size (at dehiscence) — 1. Length: Usually 0.8 to 1.0 mm. 2. Diameter: Usually 0.5 to 0.7 mm. (f) Pollen grains (at dehiscence) — 1. Diameter: 81.5±8.5 μm. 2. Percent viable pollen (estimated with fluoroscein diacetate): 85 to 95%.

D. *Gynoecium* (*pistil*).—(1) General: Pistil with compound, parietal placentation. Style slender, elongate. Stigma lobes 6–7, erect at anthesis and reflexed when mature, linear, white, papillate. (2) Style: (a) General — Slender and inserted at ovary. (b) Shape — Elongated, slender, terete. (c) Texture — Glabrous and waxy. (d) Color — White (R.H.S. 155D) at proximal end and gradually becoming fuchsia purple (R.H.S. 67B) at distal end. (e) Size (at anthesis) — 1. Length: Usually 15 to 23 mm. 2. Diameter: Usually 0.8 to 0.9 mm halfway between the proximal and distal ends. (3) Stigma: (a) General — Stigma lobes 6–7, linear, erect at anthesis but gradually becoming reflexed with age. (b) Shape — Linear with rounded apices, upper surface and sides covered with elongate papillae. (c) Texture — Fleshy. (d) Color — White (R.H.S. 155D). (e) Size — 1. Length: About 3 to 5 mm. 2. Diameter: About 0.8 mm. (4) Ovary: (a) General — Inferior, devoid of areoles, occasionally with 1 or more subulate scales, (usually) 6–7 carpels with numerous ovules. (b) Shape — Obovoid, truncate-umbiculate at the distal end, sharply 5- to 6-angled. (c) Texture — Glabrous and waxy. (d) Color — Moderate olive green (R.H.S. 137 B/C) at base and beetroot purple (R.H.S. 71A) along edges of ribs at the distal end. (e) Size — 1. Length: About 9 to 11 mm. 2. Diameter (maximum): About 8 to 10 mm.

What is claimed is:

1. A new and distinct variety of *Easter cactus* as shown and described and which is principally distinguished by the following characteristics:

a) phylloclades that are longer and wider than those of its progenitor;
b) a more erect, stiffer plant that is less prone to stem breakage than its progenitor;
c) a plant that exhibits less branching compared to its progenitor, with comparisons made on either pruned or unpruned plants;
d) flowers that are considerably larger (about 6.7 cm in diameter) compared to those of its progenitor (about 5.6 cm in diameter); and
e) flowers that remain open about 8 days, which is about 3 to 4 days less than those of its progenitor.

* * * * *